(12) United States Patent
Needham

(10) Patent No.: US 12,714,603 B2
(45) Date of Patent: Aug. 25, 2026

(54) SPORT SAFETY GLASSES

(71) Applicant: Everyman Investments, LLC, Dallas, TX (US)

(72) Inventor: Steven Anthony Needham, Dallas, TX (US)

(73) Assignee: Everyman Investments, LLC, Dallas, TX (US)

( * ) Notice: Subject to any disclaimer, the term of this patent is extended or adjusted under 35 U.S.C. 154(b) by 0 days.

(21) Appl. No.: 19/402,079

(22) Filed: Nov. 26, 2025

(65) Prior Publication Data

US 2026/0157889 A1 Jun. 11, 2026

Related U.S. Application Data

(60) Provisional application No. 63/730,923, filed on Dec. 11, 2024.

(51) Int. Cl.
*A61F 9/00* (2006.01)
*A61F 9/02* (2006.01)

(52) U.S. Cl.
CPC .................................... *A61F 9/026* (2013.01)

(58) Field of Classification Search
CPC . A61F 9/026; A61F 9/029; A61F 9/02; A42B 1/08
See application file for complete search history.

(56) References Cited

U.S. PATENT DOCUMENTS 1,954,184 A * 4/1934 Schlumbohm ........... G02C 7/16 2/433
2,914,769 A * 12/1959 Anderson ............... A61F 9/026 2/9
4,229,837 A * 10/1980 Solari ..................... A63B 71/10 2/431
4,240,718 A * 12/1980 Wichers ................. G02C 3/003 351/83
4,288,878 A * 9/1981 Helmbreck ............... A61F 9/02 2/427
4,367,561 A * 1/1983 Solari ...................... A61F 9/026 2/9
4,405,214 A 9/1983 Bolle
4,494,251 A * 1/1985 Ainsworth ............... G02C 7/16 2/443
5,682,621 A 11/1997 Park
(Continued)

*Primary Examiner* — Richale L Quinn
(74) *Attorney, Agent, or Firm* — Johnston IP Law, PLLC

(57) ABSTRACT

Sport safety glasses include a first rim portion and a second rim portion, each forming an opening for viewing therethrough. Each rim portion has a front face, inner section, outer section, upper section, and lower section. A bridge portion couples the rim portions at their inner sections. First and second support arms couple to the outer sections of the respective rim portions. Extensions project forward from the front faces of the rim portions. In one embodiment, upper and lower extensions are coupled to the upper and lower sections of each rim portion. The extensions configured to prevent balls having a predetermined diameter from passing through the openings and contacting a user's eyes. Alternative embodiments include only upper extensions positioned at angles less than 90 degrees, or unified extensions connected by a bridge extension across the front of the safety glasses.

20 Claims, 6 Drawing Sheets

(56) References Cited

U.S. PATENT DOCUMENTS

| | | | | |
|---|---|---|---|---|
| 6,848,786 | B1 * | 2/2005 | Teng | G02C 1/06 351/86 |
| 7,260,854 | B2 * | 8/2007 | Hahn | A42B 3/20 2/431 |
| 8,327,466 | B2 * | 12/2012 | Hahn | A61F 9/029 2/431 |
| D701,262 | S * | 3/2014 | Nadler | D16/326 |
| 9,314,376 | B1 * | 4/2016 | Sherer | A61F 9/029 |
| 2004/0133958 | A1 * | 7/2004 | Darnell | A63B 71/10 2/15 |
| 2009/0178185 | A1 * | 7/2009 | Brine, III | A61F 9/026 2/9 |
| 2010/0110366 | A1 | 5/2010 | Shapiro | |
| 2018/0036174 | A1 * | 2/2018 | Randolph | A61F 9/026 |
| 2022/0107512 | A1 * | 4/2022 | Messiou | G02C 7/16 |

* cited by examiner 112
100
104, 160
128
176
104, 164
108
110
116
111
152

SPORT SAFETY GLASSES

RELATED APPLICATION

This application claims the benefit of U.S. Provisional Patent Application 63/730,923 filed on Dec. 11, 2024, entitled "Sport Safety Glasses," which is incorporated herein by reference for all purposes.

TECHNICAL FIELD

This application is directed, in general, to safety glasses, and more specifically, to sport safety glasses for use in sports involving small balls, such as pickleball.

BACKGROUND

The following discussion of the background is intended to facilitate an understanding of the present disclosure only. It should be appreciated that the discussion is not an acknowledgement or admission that any of the material referred to was part of the common general knowledge at the priority date of the application.

Many sports involve balls or other objects that present eye hazards to participants. Balls may impact a participant's eye, causing injury. While sport safety glasses are known to protect participants' eyes, improvements are desired to better prevent ball impact injuries in sports such as pickleball, tennis, and racquetball.

SUMMARY

According to an illustrative embodiment, sport safety glasses include a first rim portion and a second rim portion. Each of the first rim portion and the second rim portion form an opening for viewing therethrough. Each of the first rim portion and the second rim portion has a front face, an inner section, an outer section, an upper section, and a lower section. The sport safety glasses include a bridge portion coupled to the inside section of each rim portion. A first support arm is coupled to the outside section of the first rim portion. A second support arm is coupled to the outside section of the second rim portion. At least one first extension is coupled to the front face of the first rim portion. At least one second extension is coupled to the front face of the second rim portion. The at least one first extension is sized and configured to prevent any portion of a ball having a diameter of at least 2.5 inches from passing through the opening of the first rim portion. The at least one second extension is sized and configured to prevent any portion of a ball having a diameter of at least 2.5 inches from passing through the second rim portion.

According to another illustrative embodiment, sport safety glasses include a frame having a front face, a first rim portion, a second rim portion, and bridge portion. Each rim portion forms an opening, and the bridge portion connects the first rim portion and the second rim portion. The sport safety glasses include a plurality of support arms projecting rearward from the frame in direction 107. At least one support arm extends from each of the first rim portion and the second rim portion. The sport safety glasses include a plurality of extensions projecting forward from the frame in direction 103. Each of the plurality of extensions extends from the front face of the frame a distance of 0.5-2.5 inches.

According to still another illustrative embodiment, sport safety glasses include a first rim portion and a second rim portion, each rim portion forming an opening for viewing therethrough. Each rim portion has a front face, an inner section, an outer section, an upper section, and a lower section. A bridge portion is coupled to the inner section of each rim portion. A first support arm is coupled to the outer section of the first rim portion. A second support arm is coupled to the outer section of the second rim portion. A first upper extension is coupled to the upper section of the first rim portion and extends forward from the front face of the first rim portion. A first lower extension is coupled to the lower section of the first rim portion and extends forward from the front face of the first rim portion. A second upper extension is coupled to the upper section of the second rim portion and extends forward from the front face of the second rim portion. A second lower extension is coupled to the lower section of the second rim portion and extends forward from the front face of the second rim portion. Each of the upper extensions and lower extensions has a length in the range of 0.5 to 2.5 inches. The upper extensions have a length that is greater than a length of the lower extensions. A distance between the first upper extension and the first lower extension is 3.0 inches or less.

Other embodiments are disclosed.

DESCRIPTION OF THE DRAWINGS

Illustrative embodiments of the present disclosure are described in detail below with reference to the attached drawing figures, which are incorporated by reference herein and wherein.

DETAILED DESCRIPTION

In the following detailed description of the preferred embodiments, reference is made to the accompanying drawings that form a part hereof, and in which is shown, by way of illustration, specific embodiments in which the disclosure may be practiced. These embodiments are described in sufficient detail to enable those skilled in the art to practice the disclosure, and it is understood that other embodiments may be utilized, and that logical structural, mechanical, electrical, and chemical changes may be made without departing from the spirit or scope of the disclosure. To avoid detail not necessary to enable those skilled in the art to practice the disclosure, the description may omit certain information known to those skilled in the art. The following detailed description is, therefore, not to be taken in a limiting sense, and the scope of the present disclosure is defined only by the claims. Unless otherwise indicated, as used throughout this document, "or" does not require mutual exclusivity.

Figure 1:
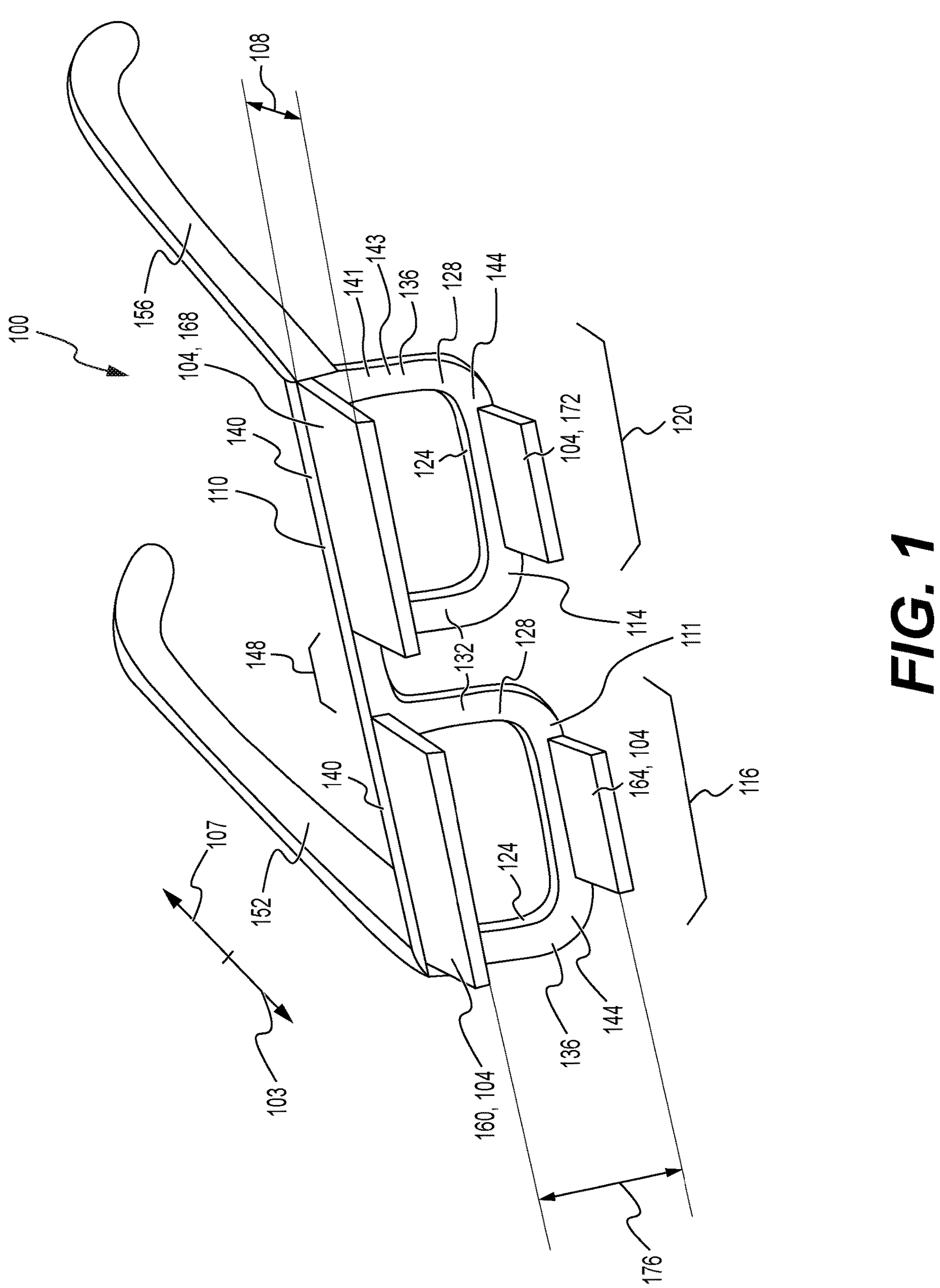
FIG. 1 is a schematic, perspective view of an illustrative embodiment of a pair of safety glasses.
Figure 2:
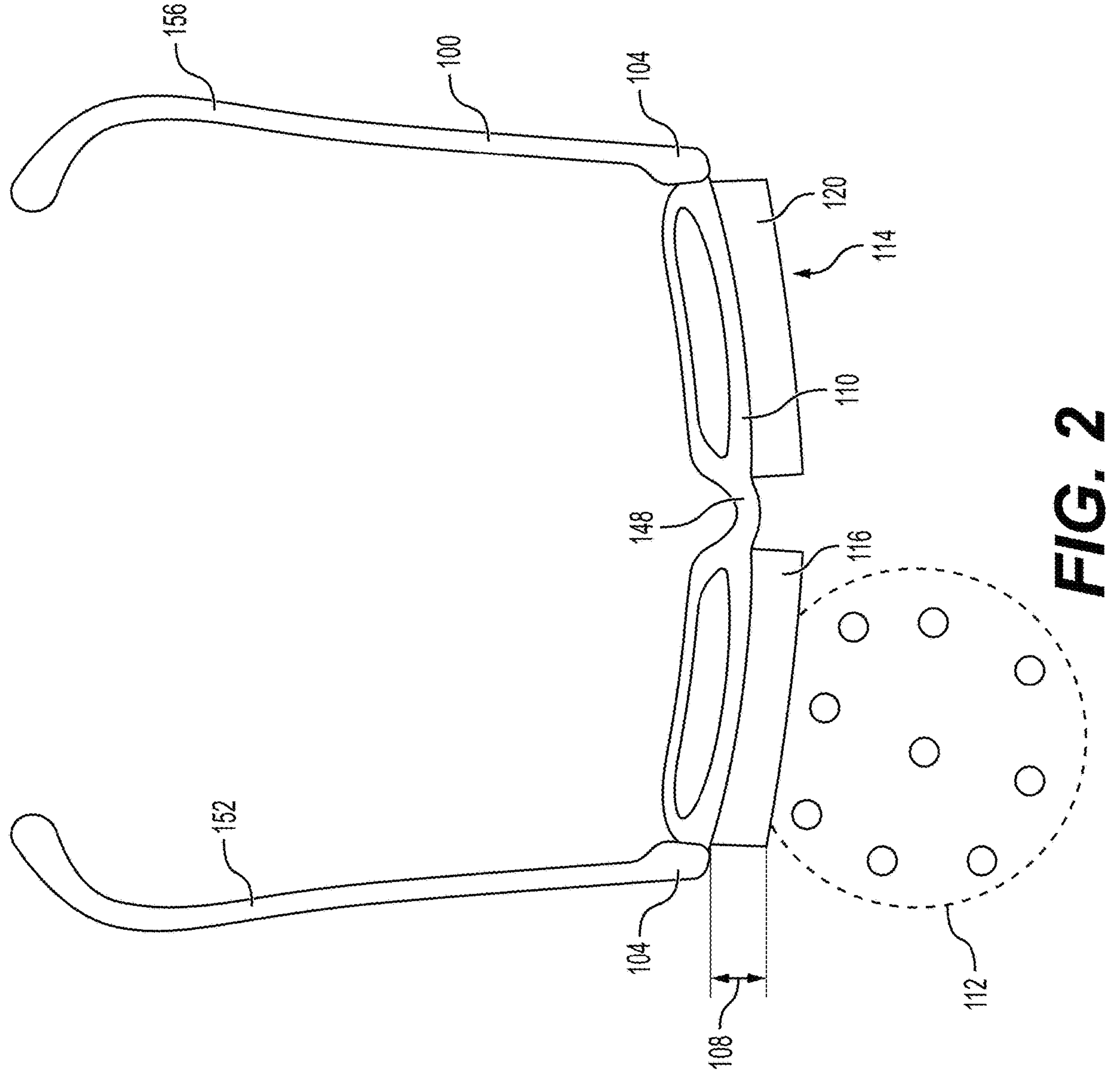
FIG. 2 is a schematic, top perspective view of an illustrative embodiment of a pair of safety glasses.
Figure 3:
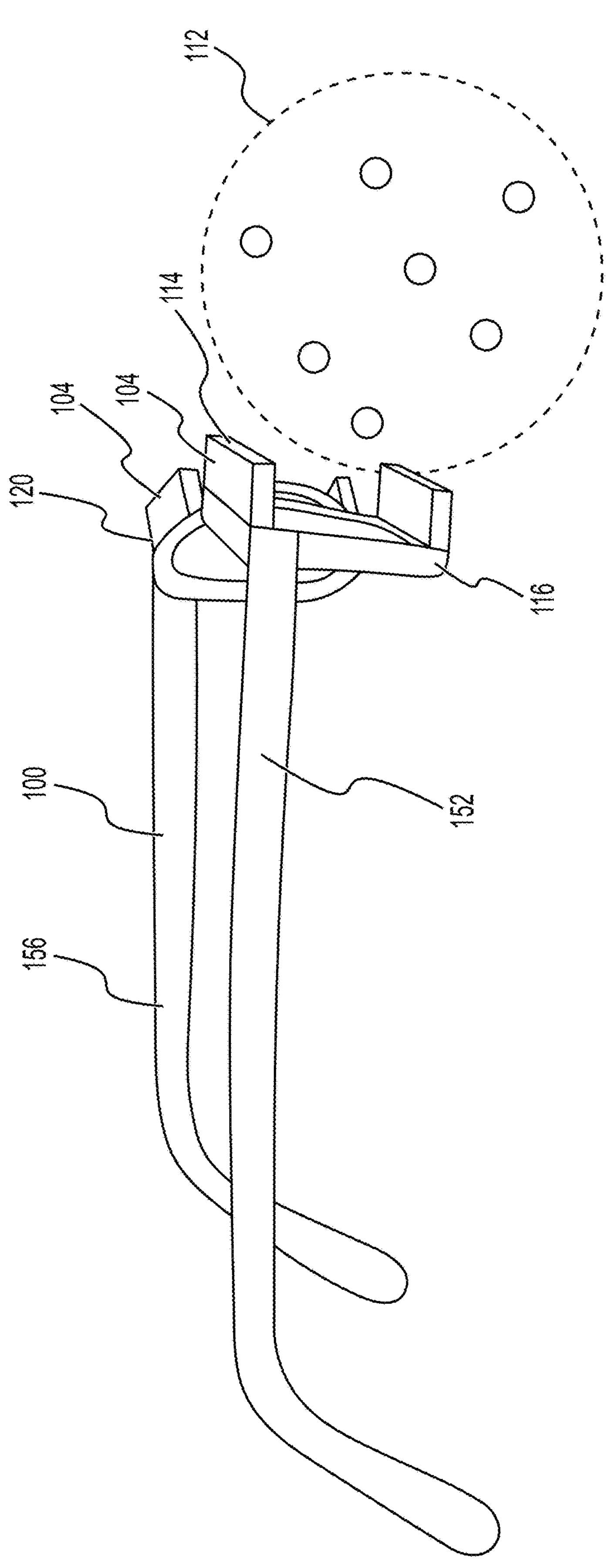
FIG. 3 is a schematic, side perspective view of an illustrative embodiment of a pair of safety glasses.

Referring now to FIGS. 1-3 and primarily to FIG. 1, an illustrative embodiment of a pair of safety glasses 100 will be described. The safety glasses 100 include a first rim portion 116 and a second rim portion 120. The first rim portion 116 and a second rim portion 120 each form an opening 124 for viewing therethrough when the safety glasses 100 are worn by a user. Each of the first rim portion 116 and the second rim portion 120 have a front face 128, an inner section 132, an outer section 136, an upper section 140, and a lower section 144.

The rim portions 116, 120 may be constructed from various materials including plastics, polymers, metals, or composite materials that provide durability while maintaining lightweight characteristics for user comfort during extended wear.

The first rim portion 116 and the second rim portion 120 are each coupled to a bridge portion 148 of the safety glasses 100 at the inner section 132 of the first rim portion 116 and the second rim portion 120 or at the upper section 140 of each of the first rim portion 116 and the second rim portion 120. When worn by a user, the bridge portion 148 sits at or near a nose of the user, the first rim portion 116 aligns with one of the user's eyes so the user can see through the opening 124 of the first rim portion 116, and the second rim portion 120 aligns with the other eye of the user so the user can see through the opening 124 of the second rim portion 120. The first rim portion 116, the second rim portion 120, and the bridge portion 148 form a frame 141 having a face 143.

The bridge portion 148 may be constructed with various configurations to accommodate different nose shapes and sizes for optimal comfort and fit. In some embodiments, the bridge portion 148 includes adjustable nose pads that can be positioned to distribute weight evenly across the user's nose bridge. The bridge portion 148 may also incorporate ventilation features or be shaped to minimize fogging when the safety glasses 100 are worn during physical activity. The coupling between the bridge portion 148 and the rim portions 116, 120 may be achieved through various means including welding, adhesive bonding, mechanical fasteners, or integral molding, depending on the materials used and manufacturing requirements.

A first support arm 152 is coupled to or proximate to the outer section 136 of the first rim portion 116 or to or proximate to the upper section 140 of the first rim portion 116. A second support arm 156 is coupled to or proximate to the outer section 136 of the second rim portion 120 or to or proximate to the upper section 140 of the second rim portion 120. The first support arm 152 and the second support arm 156 extend rearward from the frame 141. When the safety glasses 100 are worn by a user, each of the first support arm 152 and the second support arm 156 extend substantially perpendicular to the first rim portion 116 and the second rim portion 120. In some embodiments, the first support arm 152 and second support arm 156 are coupled to the first rim portion 116 and the second rim portion 120, respectively, directly or by a hinge so that the first support arm 152 and the second support arm 156 can be folded closed when not in use.

The support arms 152, 156 may be constructed from materials similar to or different from the rim portions 116, 120, and may include ergonomic features such as curved temple tips or adjustable nose pads for enhanced comfort during extended wear. The length and curvature of the support arms 152, 156 can be optimized for different head sizes and shapes to ensure a secure fit that maintains the proper positioning of the rim portions 116, 120 relative to the user's eyes. In embodiments where hinges are employed, the hinges may be spring-loaded or include detent mechanisms to provide controlled folding action and secure positioning in both open and closed configurations. The support arms 152, 156 may also incorporate grip-enhancing textures or materials to prevent slippage during physical activity and may include ventilation channels or perforations to reduce heat buildup and improve comfort during use.

The safety glasses 100 include at least one extension 104 coupled to each of the front faces 128 of the first rim portion 116 and the second rim portion 120 or the face 143. The at least one extension 104 extends forward from the front faces 128 of the first rim portion 116 and the second rim portion 120 or the face 143 of the frame 141. In the illustrative embodiment of FIG. 1, there are four extensions 104. A first upper extension 160 is coupled to the upper section 140 of the first rim portion 116. A first lower extension 164 is coupled to the lower section 144 of the first rim portion 116. A second upper extension 168 is coupled to the upper section 140 of the second rim portion 120. A second lower extension 172 is coupled to the lower section 144 of the second rim portion 120. The extensions 104 have a length 108, which determines how far out the extensions 104 extend from the front faces 128 of the first rim portion 116 and the second rim portion 120 or the face 143. In other embodiments, only the first upper extension 160 and the second upper extension 168 are used, and the first lower extension 164 and the second lower extension 172 are omitted.

The extensions 104 may be constructed from various materials including plastics, polymers, metals, or composite materials that provide durability while maintaining lightweight characteristics. In some embodiments, the extensions 104 are made from an opaque, translucent, or transparent material. In some embodiments, the extensions 104 are made from a light sensitive material that darkens when exposed to light and becomes less dark when exposed to less light.

The light sensitive material may be a polymer including a photochromic additive such as photochromic molecules or dyes, such as oxazines and naphthopyrans, that undergo a reversible structural change when exposed to light. This chemical reaction causes the material to darken. When the light source is removed, the molecules return to their original, transparent structure. In some embodiments, the photochromic additive is a microcrystalline silver halide (typically silver chloride) embedded in the material. Exposure to light causes the silver halides to form elemental silver, which is visible and darkens the materials. In the absence of light, the reaction reverses and the material clears.

In some embodiments, the extensions 104 are formed integrally with the rim portions 116, 120 during a molding process, while in other embodiments, the extensions 104 are separately manufactured and subsequently attached through welding, adhesive bonding, mechanical fasteners, or other suitable coupling methods. The extensions 104 may have various cross-sectional shapes including circular, oval, rectangular, or aerodynamic profiles to optimize both structural integrity and air resistance during physical activity. The surface of the extensions 104 may include texturing, ribbing, or other features to enhance grip or reduce glare, and may be colored or treated with coatings to improve visibility or aesthetic appeal. The extensions 104 are positioned and oriented to provide maximum ball deflection capability while minimizing obstruction of the user's peripheral vision, ensuring that the safety function does not significantly compromise the user's field of view during sports activities.

The length 108 of the extensions 104 may vary depending on their position and function. In some embodiments, the upper extensions 160, 168 have a length 108 in the range of 0.5 to 2.5 inches, while the lower extensions 164, 172 have a length 108 in the range of 0.5 to 2.5 inches. The upper extensions 160, 168 may have a length 108 that is greater than the length 108 of the lower extensions 164, 172 to provide enhanced protection from balls approaching from upper trajectories while maintaining an unobstructed lower field of view. This differential sizing allows for optimized protection based on typical ball approach angles in various sports while preserving visual access to ground-level activities and movements.

The safety glasses 100 have a distance 176 between the first upper extension 160 and the first lower extension 164 and between the second upper extension 168 and the second lower extension 172. The first upper extension 160 and the first lower extension 164; the second upper extension 168 and the second lower extension 172; and the length 108 are sized and configured so that the distance 176 is small enough to prevent a ball 112 (FIG. 2) from passing through either opening 124 or otherwise contacting the user's eye. In some embodiments, the distance 176 is small enough to prevent any portion of a ball from entering either opening 124. For example, the sport pickleball uses a ball that typically has a diameter in the range of 2.75-3.25 inches and often has a diameter in the range of 2.87-2.97 inches; the sport of tennis uses a ball that typically has a diameter in the range of 2.25-3.00 inches and often has a diameter in the range of 2.57-2.70 inches; the sport racquetball uses a ball that typically has a diameter in the range of 2.00-2.25 inches and often has a diameter in of 2.5 inches.

In some embodiments, the distance 176 is sized to prevent the ball 112 having a diameter in the range of 2-3 inches from entering the openings 124 from a front 114 (FIG. 2) of the safety glasses 100. In some embodiments, the distance 176 is sized to prevent the ball 112 having a diameter greater than 2.5 inches from entering the openings 124 from the front 114 (FIG. 2) of the safety glasses 100, i.e., far enough so that the ball 112 will not contact an eye of a user of the safety glasses 100. In some embodiments, the distance 176 is sized to prevent a standard sized pickleball from entering the openings 124 far enough so that the pickleball will contact an eye of a user of the safety glasses 100. In some embodiments, the distance 176 between the upper and lower extensions is 3.0 inches or less.

The distance 176 may be specifically configured for different sports and their corresponding ball sizes. For pickleball applications, where balls typically have diameters ranging from 2.75 to 3.25 inches, the distance 176 may be configured to be less than 2.5 inches, and in some embodiments between 1.5 to 2.25 inches, to ensure adequate ball deflection while maintaining sufficient field of view. For tennis applications, where balls typically have diameters ranging from 2.57 to 2.70 inches, the distance 176 may be configured to be less than 2.25 inches, and in some embodiments between 1.25 to 2.0 inches. For racquetball applications, where balls typically have diameters around 2.25 inches, the distance 176 may be configured to be less than 2.0 inches, and in some embodiments between 1.0 to 1.75 inches. The specific distance 176 selected may also account for the approach angle of the ball, the extension length 108, and the desired balance between protection and peripheral vision. In multi-sport embodiments, the distance 176 may be optimized for the smallest ball diameter expected to be encountered, ensuring comprehensive protection across different sporting activities.

The extensions 104 are configured to allow the ball 112 to approach the user's eyes beyond the extensions 104 without contacting the user's eyes. In some embodiments, the ball 112 may partially enter the openings 124 or pass beyond the plane of the extensions 104 while still being prevented from making contact with the user's eyes due to the geometric relationship between the extensions 104, the distance 176, the length 108, and the ball diameter. The extensions 104 function as deflection barriers that redirect the ball's trajectory or create physical interference that prevents the ball 112 from reaching the user's eyes, even when the ball 112 penetrates into the space between the extensions 104. This configuration allows for a larger field of view while maintaining eye protection, as the critical safety requirement is preventing eye contact rather than completely excluding the ball 112 from the area in front of the safety glasses 100.

In some embodiments, all of the extensions 104 have the same shape and size. In some embodiments, the extensions 104 have different sizes or shapes. In some embodiments, only the first upper extension 160 and the second upper extension 168 are used and the first lower extension 164 and second lower extension 172 are omitted. See, e.g., FIG. 5. In some embodiments, the first upper extension 160 and the second upper extension 168 are coupled to a bridge extension 175 (See FIG. 6) to form a unified extension across the front 114 of the safety glasses.

The extensions 104 may vary in configuration to accommodate different sports, user preferences, and manufacturing considerations. In some embodiments, the extensions 104 are removable or interchangeable, allowing users to customize the protection level based on the specific sport being played or personal comfort preferences. The extensions 104 may include cushioning or padding materials at contact points to reduce impact forces when struck by a ball 112, and may incorporate shock-absorbing properties to dissipate energy upon impact. Some embodiments may feature adjustable extensions 104 that can be repositioned or resized to optimize the balance between protection and field of view for individual users. The extensions 104 may also include visual indicators, markings, or color coding to assist users in proper positioning and to enhance visibility of the safety glasses 100 during use. In certain embodiments, the extensions 104 may be designed with aerodynamic profiles to minimize wind resistance during physical activity and may include drainage features or surface treatments to prevent water or sweat accumulation that could affect visibility or comfort.

In some embodiments, one or more of the extensions 104 is coupled to a top edge 110 or to a lower edge 111 of the safety glasses 100 instead of being coupled to the front face 128 of the first rim portion 116 or the second rim portion 120.

In some embodiments, the safety glasses or the extensions 104 are formed from a translucent material, such as a plastic or other polymer, to increase user visibility during use of the safety glasses 100.

The safety glasses 100 and extensions 104 may be constructed from a wide variety of materials selected based on durability, weight, optical properties, and manufacturing requirements. Suitable materials include various plastics such as polycarbonate, which offers excellent impact resistance and optical clarity; acrylic (PMMA), which provides good transparency and weather resistance; polyethylene terephthalate (PET), which offers chemical resistance and dimensional stability; and thermoplastic polyurethane (TPU), which provides flexibility and impact absorption. Other polymer options include nylon, which offers high strength-to-weight ratios; polypropylene, which provides chemical resistance and low cost; and various copolymers that can be tailored for specific mechanical and optical properties. Metal components may include aluminum alloys for lightweight strength, titanium for corrosion resistance and biocompatibility, stainless steel for durability, and various metal alloys that can be anodized or coated for enhanced appearance and protection. Composite materials such as carbon fiber reinforced polymers may be employed for high-performance applications requiring maximum strength and minimum weight. The materials may be transparent, translucent, or opaque depending on the specific component and functional requirements, with transparent or translucent materials being preferred for components that may obstruct the user's field of view. Surface treatments such as anti-reflective coatings, scratch-resistant coatings, UV-protective coatings, or anti-fog treatments may be applied to enhance performance and durability. The material selection may also consider factors such as hypoallergenicity for skin contact areas, ease of cleaning and sterilization, and environmental considerations such as recyclability or biodegradability.

Figure 4:
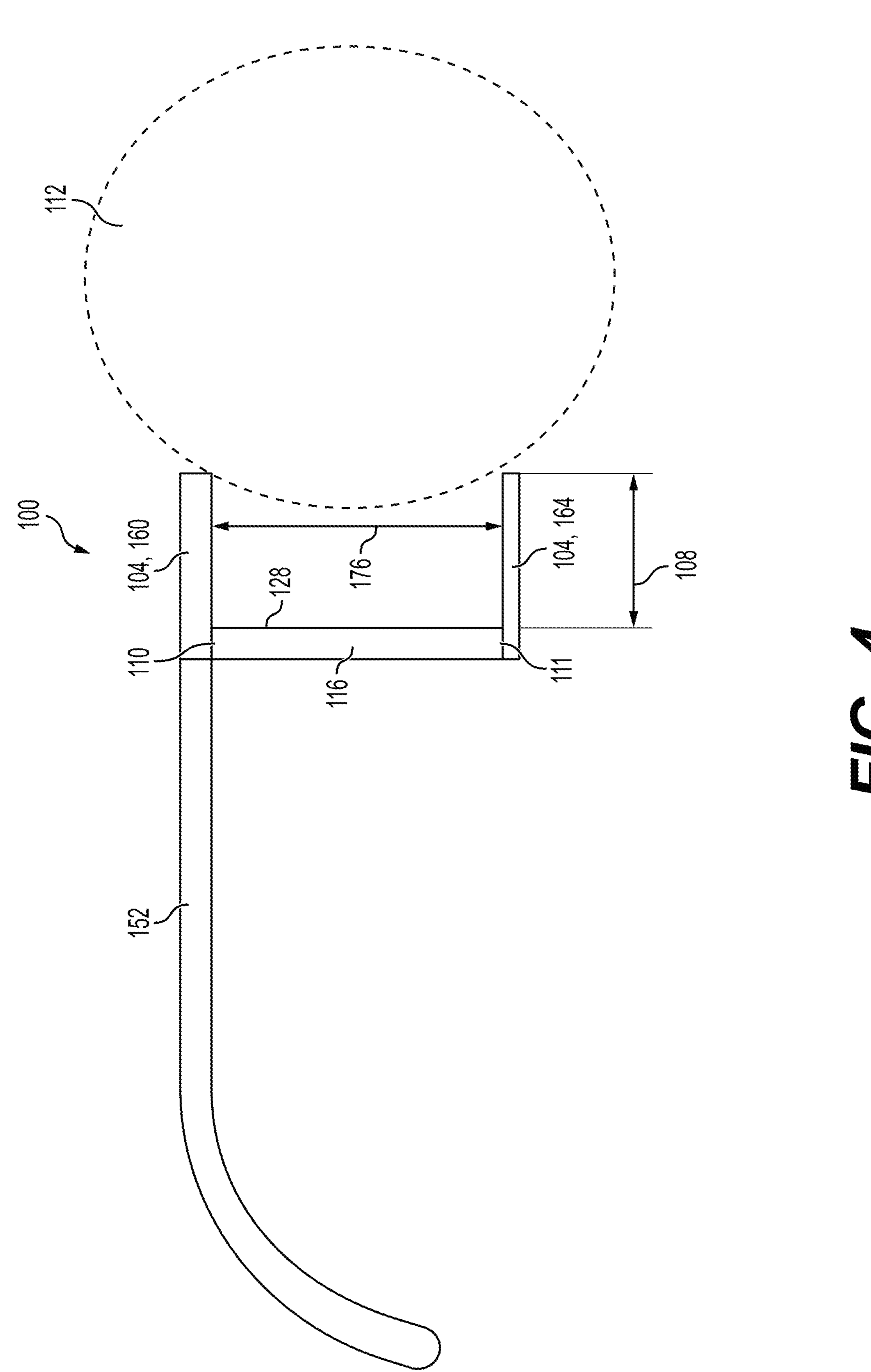
FIG. 4 is a schematic, side view of an illustrative embodiment of a pair of safety glasses.

Referring now primarily to FIG. 4, an illustrative embodiment of the safety glasses 100 will be discussed. The illustrative embodiment of the safety glasses 100 of FIG. 4 is analogous to the illustrative embodiment of the safety glasses 100 of FIGS. 1-3 in most aspects. The safety glasses 100 of FIG. 4 vary in that the extensions 104 are coupled to the top edge 110 or lower edge 111 of the safety glasses 100, as opposed to being coupled to the front face 128 of the first rim portion 116 or second rim portion 120. The distance 176 and length 108 are sized so that the ball 112 contacts the extensions 104 prior to entering the openings 124 (FIG. 1) of the safety glasses 100. Therefore, the extensions 104 work to prevent contact between the ball 112 and an eye of a person wearing the safety glasses 100.

Figure 5:
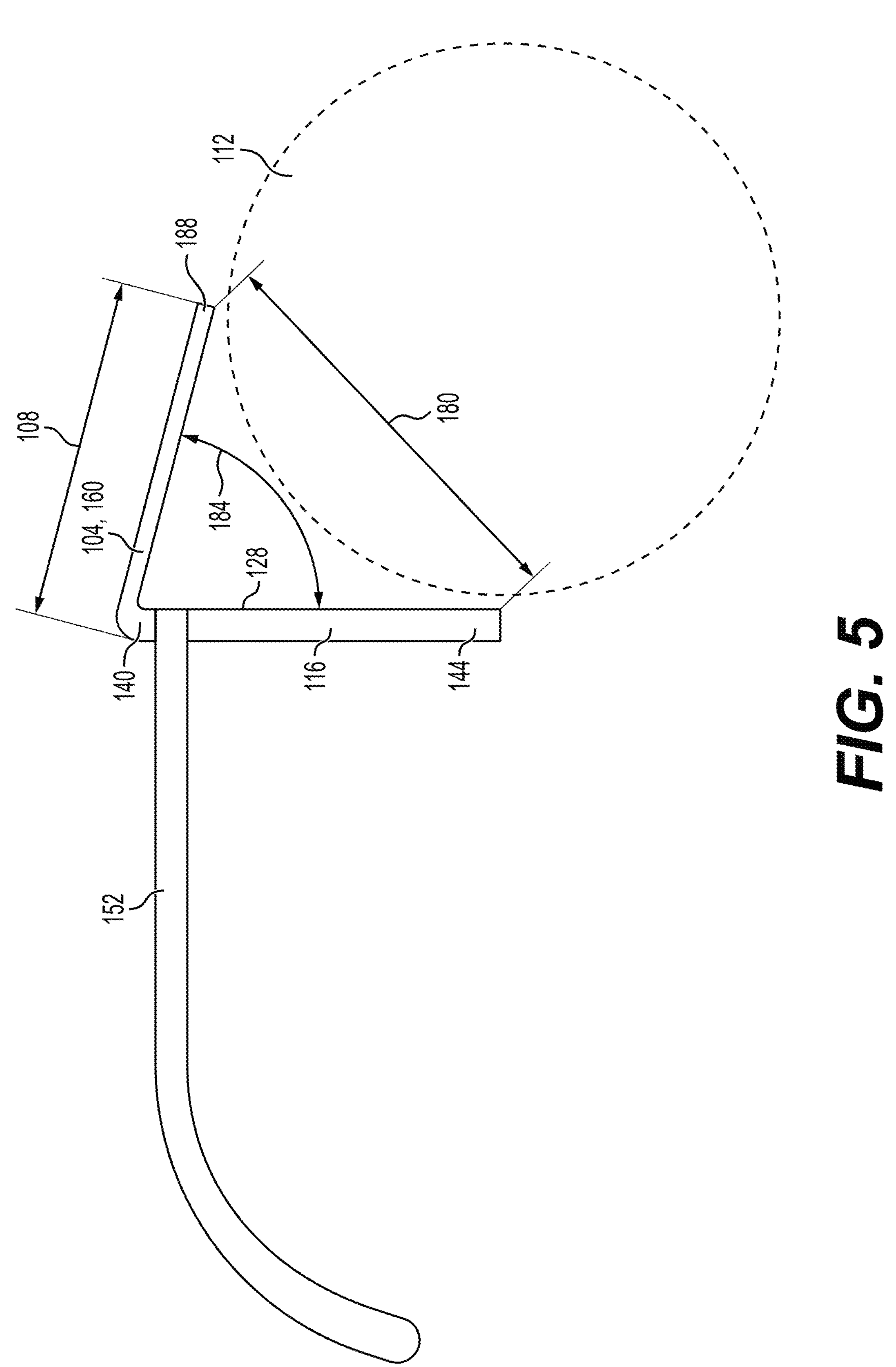
FIG. 5 is a schematic, side view of an illustrative embodiment of a pair of safety glasses.

Referring now primarily to FIG. 5, an illustrative embodiment of the safety glasses 100 will be discussed. The illustrative embodiment of the safety glasses 100 of FIG. 5 is analogous to the illustrative embodiment of the safety glasses 100 of FIGS. 1-3 in some aspects. The safety glasses 100 of FIG. 5 vary in some respects that will be discussed. The safety glasses 100 of FIG. 5 omit the first lower extension 164 and second lower extension 172 (FIG. 1). The first upper extension 160 and the second upper extension 168 are coupled to the first rim portion 116 and the second rim portion 120, respectively, at an angle 184, which is in some embodiments is between 75-100 degrees. In some embodiments the angle 184 is about 90 degrees. In some embodiments the angle 184 is less than 90 degrees relative to the front 114 of the safety glasses 100. In some embodiments the angle 184 is in the range of 70-85 degrees. The safety glasses 100 have a distance 180 between the extended edge 188 of the first upper extension 160 or the second upper extension 168 and the lower section 144 of the first rim portion 116 or the second rim portion 120. In some embodiments, the distance 180 is 3.0 inches or less.

In the embodiment of FIG. 5, the length 108 and angle 184 are sized and configured so that the ball 112 cannot enter the openings 124 (FIG. 1) of the first rim portion 116 or second rim portion 120.

Continuing to refer to FIG. 5, in some embodiments, the angle 184 may be 90 degrees or even larger, as long as the geometry provides for the dimension 180 to be such that the ball 112 cannot contact the user's eyes. For example, angle 184 may be 90 degrees and the upper extension 104, 160 extend far enough out in front such that when the ball 112 contacts the upper extension 160, 168 and the lower sections 144 of the rim portions 116, 120, the ball 112 will be prevented from contacting the user's eyes.

Returning again to FIG. 1, note that the upper extensions 160, 168 may be a unitary member that extends across the front of the glasses 100 with no break at the nose area. The bottom extensions 164, 172 may extend the width of the rims on each side. As suggested in FIG. 5, the lower extensions 164, 172 may be excluded, and the top extensions 160, 168 made long enough vis-à-vis dimension 108 to keep the ball 112 out based on the geometry of the upper extensions 164, 172 and the lower sections 144 of the rim portions 116, 120. In some embodiments, the rims 116, 120 may be partial or have breaks in them at certain locations.

Figure 6:
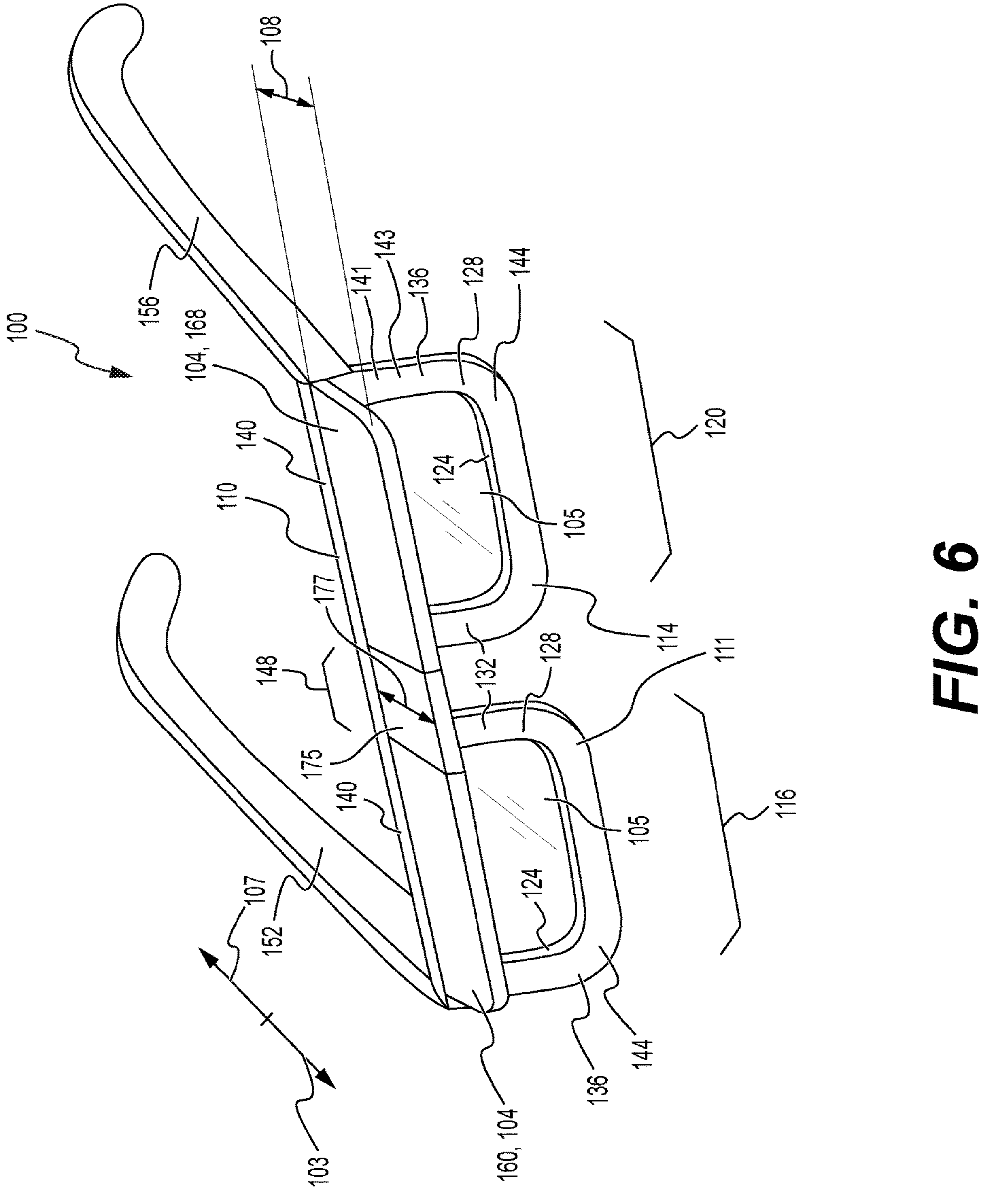
FIG. 6 is a schematic, perspective view of an illustrative embodiment of a pair of safety glasses.

Referring now to FIG. 6, an alternative embodiment of the safety glasses 100 will be discussed. The embodiment of the safety glasses 100 of FIG. 6 are analogous to the safety glasses 100 of FIGS. 1-3 in many regards. The differences will be discussed. The safety glasses 100 of FIG. 6 includes a bridge extension 175. The bridge extension 175 extends from the bridge portion 148. In addition, the bridge extension 175 is joined on one side to the first upper extension 160 and on the opposite side to the second lower extension 164. In this manner, the first upper extension 160, the first lower extension 164, and bridge extension 175 form a continuous barrier across the upper portion of the safety glasses 100. In addition, the bridge extension 175 has a length 177 which defines how far the bridge extension extends from the face 114 of the safety glasses 100, from the front faces 128 of the first rim portion 116 and the second rim portion 120 or the face 143. In some embodiments the length 175 of the bridge extension 175 is equal to the length 108 of the extensions 104. In some embodiments, the bridge extension 175 is less than the length 108 of the extensions 104.

The bridge extension 175 provides additional protection across the central area between the rim portions 116, 120, creating a more comprehensive barrier against ball 112 impact. In some embodiments, the bridge extension 175 may be removable or adjustable to accommodate different user preferences or sport-specific requirements. The bridge extension 175 may be constructed from the same materials as the other extensions 104 or may utilize different materials optimized for its specific positioning and function. For example, the bridge extension 175 may incorporate softer materials or padding where it might contact the user's nose area during impact events. The bridge extension 175 may also include ventilation features, perforations, or channels to promote airflow and reduce fogging of any lenses 105 that may be present. In embodiments where the bridge extension 175 connects the upper extensions 160, 168, the resulting unified structure provides enhanced structural integrity and more uniform load distribution when impacted by a ball 112. The bridge extension 175 may be angled or curved to optimize both protective coverage and aesthetic appearance and may include surface texturing or treatments to reduce glare or improve visibility. Some embodiments may feature the bridge extension 175 that extends at a different angle 184 compared to the side extensions 104, allowing for customized protection profiles based on the specific sport or user requirements. The bridge extension 175 may also serve as a mounting point for additional accessories such as sweat guards, impact indicators, or identification markings.

In the embodiment shown in FIG. 6, the lower extensions 164, 172 are omitted, with the safety glasses 100 relying on the upper extensions 160, 168 and the bridge extension 175 for ball protection. In some embodiments, the bridge extension 175 is also omitted. This configuration creates a continuous protective barrier across the upper portion of the safety glasses 100, extending from the first upper extension 160, through the bridge extension 175, to the second upper extension 168. The absence of lower extensions 164, 172 provides an unobstructed lower field of view, which may be advantageous for sports requiring enhanced downward visibility. In this embodiment, the length 108 of the upper extensions 160, 168 and the length 177 of the bridge extension 175 are configured to work in conjunction with the lower sections 144 of the rim portions 116, 120 to prevent ball 112 contact with the user's eyes. The geometric relationship between the extended upper barrier and the lower rim sections 144 creates an effective protective zone that deflects or blocks balls 112 approaching from various angles. This design may be particularly suitable for sports where balls 112 typically approach from upper trajectories, such as certain serves or overhead shots in tennis or pickleball. The unified upper extension structure also provides enhanced structural integrity compared to separate extension elements, potentially offering improved durability and more consistent protection across the central vision area. The elimination of lower extensions 164, 172 may also reduce the overall weight of the safety glasses 100 and provide a less obstructed aesthetic appearance while maintaining the essential protective function.

In some embodiments, the length 177 and the length 108 are the same. In some embodiments, the length 177 is less than the length 108. In some embodiments, the length 108 is at least twice as long as the length 177. In some embodiments, the length 177 is 20 percent or less of the length 108.

The safety glasses 100 may include lenses 105 (FIG. 6) positioned within the openings 124 of the first rim portion 116 and the second rim portion 120, or alternatively, may be configured without lenses 105 (FIG. 1) to provide an unobstructed field of view. In embodiments with lenses 105, the lenses 105 may be clear, tinted, polarized, or have other optical properties suitable for the intended sport or activity. The lenses 105, when present, may be constructed from various materials selected for their optical clarity, impact resistance, and safety characteristics. Polycarbonate lenses 105 are particularly preferred for sports applications due to their impact resistance, being virtually shatterproof and capable of withstanding high-velocity impacts without fragmenting. Trivex lenses 105 offer similar impact resistance with enhanced optical clarity and lighter weight. For applications requiring maximum safety, laminated lenses 105 comprising multiple layers with interlayer films can be employed to ensure that even if cracking occurs, the lens 105 remains intact and fragments are contained. The lenses 105 may incorporate various optical treatments including anti-reflective coatings to reduce glare, scratch-resistant hard coatings for durability, and hydrophobic coatings to repel water and sweat. Photochromic lenses 105 that automatically darken in bright light conditions may be utilized for outdoor sports, while polarized lenses 105 can reduce glare from reflective surfaces such as courts or water. Tinting options include neutral gray tints that reduce overall light transmission without color distortion, amber or yellow tints that enhance contrast in low-light conditions, and sport-specific tints optimized for particular playing surfaces or lighting conditions. The lenses 105 may also incorporate UV protection to shield the eyes from harmful ultraviolet radiation during outdoor activities. In some embodiments, the lenses 105 are designed to be easily replaceable, allowing users to swap between different tint levels or optical properties based on playing conditions or personal preferences.

It should be appreciated that the various features of the safety glasses 100 described in relation to FIGS. 1-6 may be used to form other embodiments. For example, one embodiment may include first upper extension 160 and the second upper extension 168 while omitting the first lower extension 164 and the second lower extension 172 (as shown in FIG. 6) while omitting the bridge extension 175 (as shown in FIG. 1). Other combinations of features described herein are possible.

Although the present disclosure and its advantages have been disclosed in the context of certain illustrative, non-limiting embodiments, it should be understood that various changes, substitutions, permutations, and alterations can be made without departing from the scope of the disclosure as defined by the claims. It will be appreciated that any feature that is described in a connection to any one embodiment may also be applicable to any other embodiment.

What is claimed:

1. Sport safety glasses comprising:

a first rim portion;

a second rim portion;

wherein each of the first rim portion and the second rim portion form an opening for viewing therethrough;

wherein each of the first rim portion and the second rim portion has a front face, an inner section, an outer section, an upper section, and a lower section;

a bridge portion coupled to the inside section of each rim portion;

a first support arm coupled to the outside section of the first rim portion;

a second support arm coupled to the outside section of the second rim portion;

at least one first extension coupled to the front face of the first rim portion, wherein the at least one first extension comprises a substantially planer member that extends from the upper section or the lower section of the first rim portion to a distance in front of the front face of the first rim portion without extending into or being disposed within the opening of the first rim portion, and wherein the at least one first extension is oriented substantially parallel to the upper section or the lower section of the first rim portion;

at least one second extension coupled to the front face of the second rim portion;

wherein the at least one second extension comprises a substantially planer member that extends from the upper section or the lower section of the second rim portion to a distance in front of the front face of the second rim portion without extending into or being disposed within the opening of the second rim portion, and wherein the at least one second extension is oriented substantially parallel to the upper section or the lower section of the second rim portion;

wherein the at least one first extension is sized and configured to provide a deflection barrier wherein contact between a ball having a diameter of at least 2.5 inches and the at least one first extension prevents the ball from entering into the opening of the first rim portion without preventing all of the ball from entering into a space between the front face of the first rim portion and an end of the at least one first extension that extends the distance in front of the front face of the first rim portion; and wherein the at least one second extension is sized and configured to provide a deflection barrier wherein contact between the ball and the at least one second extension prevents the ball from entering into the opening of the second rim portion without preventing all of the ball from entering into a space between the front face of the second rim portion and an end of the at least one second extension that extends the distance in front of the front face of the second rim portion.

2. The sport safety glasses of claim 1,
wherein the at least one first extension and the at least one second extension each comprise an upper and lower extension;
wherein the upper extension of the at least one first extension is coupled to the upper section of the first rim portion;
wherein the upper extension of the at least one second extension is coupled to the upper section of the second rim portion;
wherein the lower extension of the at least one first extension is coupled to the lower section of the first rim portion; and
wherein the lower extension of the at least one second extension is coupled to the lower section of the second rim portion.

3. The sport safety glasses of claim 1, wherein:
the at least one first extension comprises an upper extension coupled to the upper section of the first rim portion at a first angle that is greater than 70 degrees and less than 90 degrees relative to the front face of the first rim portion; and
the at least one second extension comprises an upper extension coupled to the upper section of the second rim portion at a second angle that is greater than 70 degrees and less than 90 degrees relative to the front face of the second rim portion.

4. The sport safety glasses of claim 3, wherein the first angle and the second angle are in the range of 75-85 degrees.

5. The sport safety glasses of claim 1, further comprising:
a bridge extension coupled to the bridge portion; and
wherein the bridge extension is coupled to the at least one first extension and to the at least one second extension to form a unified extension across an upper front face of the sport safety glasses.

6. The sport safety glasses of claim 5, wherein the bridge extension extends from the bridge portion a distance that is equal to the distance that the at least one first extension extends from the first rim portion and that is equal to the distance that the at least one second extension extends from the second rim portion.

7. The sport safety glasses of claim 5, wherein the bridge extension extends from the bridge portion a distance that is less than the distance that the at least one first extension extends from the first rim portion and that is less than the distance that the at least one second extension extends from the second rim portion.

8. The sport safety glasses of claim 1, wherein the at least one first extension and the at least one second extension are constructed from a translucent material.

9. The sport safety glasses of claim 1,
wherein the at least one first extension extends from the front face of the first rim portion in the range of 0.5 to 2.5 inches; and
wherein the at least one second extension extends from the front face of the second rim portion in the range of 0.5 to 2.5 inches.

10. The sport safety glasses of claim 1, further comprising lenses positioned within the openings of the first rim portion and the second rim portion.

11. Sport safety glasses comprising:
a frame having a front face, a first rim portion, a second rim portion, and bridge portion, wherein each rim portion forms an opening, and the bridge portion connects the first rim portion and the second rim portion;
a plurality of support arms projecting rearward from the frame, wherein at least one support arm extends from each of the first rim portion and the second rim portion;
wherein, when the sport safety glasses are worn by a user, the frame has a length that spans across the user's face in a direction that is perpendicular to the user's face wherein the opening of the first rim portion aligns with a first eye of the user and the opening of the second rim portion aligns with a second eye of the user;
a plurality of extensions coupled to the front face of the frame and projecting forward from the frame;
wherein each of the plurality of extensions extends from the front face of the frame a distance of 0.5-2.5 inches;
wherein each of the plurality of extensions are substantially planer members that are oriented substantially parallel to the length of the frame;
wherein each extension of the plurality of extensions is coupled to the front face of the frame above or below the opening of the first rim portion or the opening of the second rim portion;
wherein each extension of the plurality of extensions does not enter into the opening of the first rim portion or the opening of the second rim portion; and
wherein at least one extension of the plurality of extensions is sized and configured to provide a deflection barrier wherein contact between a ball having a diameter of at least 2.5 inches and the at least one extension prevents the ball from entering into the opening of the first rim portion or the opening of the second rim portion.

12. The sport safety glasses of claim 11, wherein the plurality of extensions comprise upper extensions and lower extensions positioned on the first rim portion or second rim portion.

13. The sport safety glasses of claim 12, wherein the upper extensions extend from the front face of the frame further than the lower extensions extend from the front face of the frame.

14. The sport safety glasses of claim 11, wherein the plurality of extensions comprise only upper extensions positioned on the first rim portion or second rim portion above the openings of the first rim portion or second rim portion.

15. The sport safety glasses of claim 11, further comprising lenses positioned within the openings of the first rim portion and the second rim portion.

16. The sport safety glasses of claim 11, wherein the plurality of extensions are configured to prevent a ball having a diameter of at least 2.5 inches from contacting a user's eyes.

17. The sport safety glasses of claim 11, wherein the ball is prevented from entering into the opening of the first rim portion or the opening of the second rim portion without preventing a portion of the ball from entering into a space between a front face of the first rim portion or of the second rim portion and an end of the at least one extension that extends the distance from the front face of the frame.

18. The sport safety glasses of claim 11, wherein each of the plurality of extensions extends from the front face of the frame a distance of 1.0-2.0 inches.

19. Sport safety glasses comprising:
a first rim portion and a second rim portion, each rim portion forming an opening for viewing therethrough;
each rim portion having a front face, an inner section, an outer section, an upper section, and a lower section;
a bridge portion coupled to the inner section of each rim portion;

a first support arm coupled to the outer section of the first rim portion;

a second support arm coupled to the outer section of the second rim portion;

a first upper extension coupled to the upper section of the first rim portion and extending forward from the front face of the first rim portion;

a first lower extension coupled to the lower section of the first rim portion and extending forward from the front face of the first rim portion;

a second upper extension coupled to the upper section of the second rim portion and extending forward from the front face of the second rim portion;

a second lower extension coupled to the lower section of the second rim portion and extending forward from the front face of the second rim portion;

wherein the first upper extension is a substantially planer member that extends a distance from the front face of the first rim portion and that is oriented substantially parallel to the upper section of the first rim portion;

wherein the first lower extension is a substantially planer member that extends a distance from the front face of the first rim portion and that is oriented substantially parallel to the lower section of the first rim portion;

wherein the second upper extension is a substantially planer member that extends a distance from the front face of the second rim portion and that is oriented substantially parallel to the upper section of the second rim portion;

wherein the second lower extension is a substantially planer member that extends a distance from the front face of the second rim portion and that is oriented substantially parallel to the lower section of the second rim portion;

wherein the distance that the first upper extension and the first lower extension extend forward from the front face of the first rim portion is in the range of 0.5 to 2.5 inches;

wherein the distance that the second upper extension and the second lower extension extend forward from the front face of the second rim portion is in the range of 0.5 to 2.5 inches;

wherein the first upper extension extends from the front face of the first rim portion further than the first lower extension;

wherein the second upper extension extends from the front face of the second rim portion further than the second lower extension;

wherein a distance between the first upper extension and the first lower extension is 3.0 inches or less;

wherein the first upper extension is sized and configured to provide a deflection barrier wherein contact between a ball having a diameter of at least 2.5 inches and the first upper extension prevents the ball from entering into the opening of the first rim portion without preventing all of the ball from entering into a space between the front face of the first rim portion and an end of the first upper extension that extends the distance from the front face of the first rim portion;

wherein the second upper extension is sized and configured to provide a deflection barrier wherein contact between the ball and the second upper extension prevents the ball from entering into the opening of the second rim portion without preventing all of the ball from entering into a space between the front face of the second rim portion and an end of the second upper extension that extends the distance from the front face of the second rim portion.

20. The sport safety glasses of claim 19, wherein each of the first upper extension and the first lower extension, extend from the first rim portion in the range of 1.0 to 2.0 inches and wherein each of the second upper extension and the second lower extension extend from the second rim portion in the range of 1.0 to 2.0 inches.

* * * * *